United States Patent
Pappagallo

(10) Patent No.: US 7,875,597 B2
(45) Date of Patent: Jan. 25, 2011

(54) TREATMENT OF SPINAL MECHANICAL PAIN

(75) Inventor: Marco Pappagallo, New York, NY (US)

(73) Assignee: New York University

( * ) Notice: Subject to any disclaimer, the term of this patent is extended or adjusted under 35 U.S.C. 154(b) by 951 days.

(21) Appl. No.: 10/624,942

(22) Filed: Jul. 21, 2003

(65) Prior Publication Data

US 2004/0087551 A1 May 6, 2004

Related U.S. Application Data

(60) Provisional application No. 60/398,175, filed on Jul. 24, 2002.

(51) Int. Cl.
*A61K 31/675* (2006.01)
*A61K 31/66* (2006.01)
(52) U.S. Cl. .................. 514/89; 514/102; 514/108
(58) Field of Classification Search .............. 514/108, 514/89, 102
See application file for complete search history.

(56) References Cited

U.S. PATENT DOCUMENTS 6,676,970 B2 * 1/2004 Bader et al. ................. 424/488
2004/0063670 A1 * 4/2004 Fox et al. .................... 514/102

OTHER PUBLICATIONS

Geusens et al. Recovery from severe Glucocorticoid-induced osteoporosis in an Adolescent Boy. Journal of Clinical Densitometry. vol. 4, p. 389-394, Winter 2001.*
Urban et al. Antinociceptive effects of the bisphosphonate, zoledronate, in a novel rat model for bone cancer pain. Society for Neuroscience Abstracts, 2001 vol. 27, No. 1 p. 1326.*
Marco Pappagallo, et al., "Treatment of Chronic Mechanical Spinal Pain with Intravenous Pamidronate: A Review of Medical Records", Journal of Pain and Symptom Management, vol. 26, No. 1, Jul. 1, 2003.

* cited by examiner

*Primary Examiner*—Jennifer M Kim
(74) *Attorney, Agent, or Firm*—Fish & Richardson P.C.

(57) ABSTRACT

The invention is directed to a method of treating chronic spinal mechanical pain by intravenous administration to a subject in need of chronic spinal mechanical pain relief of an effective amount of bisphosphonate.

6 Claims, No Drawings

TREATMENT OF SPINAL MECHANICAL PAIN

FIELD OF THE INVENTION

The invention is directed to a method of treating back pain with intravenous bisphosphonates.

BACKGROUND OF THE INVENTION

Back pain is one of the most common and often debilitating conditions affecting millions of people in all walks of life. It is estimated that over ten million people in the United States alone suffer from persistent back pain. Approximately half of those suffering from persistent back pain are afflicted with chronic disabling pain, sometimes referred to as chronic mechanical back pain, which seriously compromises the patient's quality of life and is the second most common cause of worker absenteeism. Furthermore, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on health care expenditures.

Chronic mechanical back pain has taken on many connotations by those skilled in the art. Chronic back pain has been defined as back pain that lasts for longer than 12 weeks. Others define chronic back pain as pain that lasts beyond the expected period of healing, and recognize that chronic pain may not have well-defined underlying pathological causes. Still others classify frequently recurring back pain as chronic pain since it intermittently affects an individual over a long period of time.

Approximately 97% of adult patients with low back pain have mechanical pain of non-cancer origin. In the majority of these patients, except for the presence of spondylotic disease, a precise pathoanatomical diagnosis cannot be identified. While risk factors include twisting and heavy lifting, obesity, bodily vibration, and poor conditioning, low back pain is common in people without these risk factors.

Treatment interventions vary widely among clinicians, and the most common therapeutic approaches either lack scientific evidence or are reported to be ineffective. It has been reported that most patients with low back pain in primary care will have stopped consulting about symptoms within three months after their initial consultation, but a third or more will still be experiencing low back pain and related disability one year after consultation.

The most costly services for low back pain are diagnostic procedures, surgery, and physical therapy. The most commonly used medications for chronic back pain are the non-steroidal anti-inflammatory drugs (NSAIDs), muscle relaxants, and opioid agents. These medications are of little or no value in alleviating the relatively high pain levels associated with spinal mechanical pain. Wide variations in the care of chronic low back pain suggest that there is professional uncertainty about the optimal approach, and attempts to prevent its occurrence have been unsuccessful. Because chronic pain problems do not respond reliably to many of the strategies used for the treatment of acute pain, and because inappropriate care for chronic pain conditions often leads to clinical exacerbation and increased suffering and disability, relatively non-invasive treatments specific for the relief of refractory back pain are needed to fulfill an urgent public health need.

Oral bisphosphonates are used in the treatment of osteoporosis and Paget's disease. They are poorly absorbed and often cause upper gastrointestinal toxicity.

Pamidronate, a bisphosphonate, having the formula $C_3H_9NO_7P_2Na_25H_2O$, has been administered intravenously for malignant hypercalcemia, severe osteoporosis with compression fractures, Paget's disease, and in the management of pathological fractures and bone pain secondary to metastatic cancer. The principal pharmacologic action of pamidronate is inhibition of bone resorption. Although the mechanism of antiresorptive action is not completely understood, several factors are thought to contribute to this action. Pamidronate adsorbs to calcium phosphate (hydroxyapatite) crystals in bone and may directly block dissolution of this mineral component of bone. In vitro studies also suggest that inhibition of osteoclast activity contributes to inhibition of bone resorption. In animal studies, at doses recommended for the treatment of hypercalcemia, pamidronate inhibits bone resorption apparently without inhibiting bone formation and mineralization. Pamidronate inhibits the accelerated bone resorption that results from osteoclast hyperactivity induced by various tumors in animal studies.

The recommended dose of pamidronate in moderate hypercalcemia is 60 to 90 mg, with dosages of 90 mg needed to treat severe hypercalcemia. For Paget's, the recommended dose of pamidronate is 30 mg daily, administered as a 4 hour infusion on 3 consecutive days for a total dose of 90 mg. For the management of pathological fractures and bone pain from metastatic cancer, pamidronate needs to be administered every 2-3 weeks in order to provide sustained pain relief.

Recently, it has been suggested that bisphosphonate may have a pharmacological role in the modulation of nociceptive pain, even in conditions unrelated to accelerated osteolysis or bone disease, with a possible, more general clinical application to pain control.

In 1999, Goicoechea et al. reported that alendronate, a bisphosphonate, injected intraperitoneally in mice, was able to reduce visceral pain induced by the administration of acetic acid into the abdomen. However, the doses that induced analgesia were close to those that induce toxicity.

In 2001, Bonabello et al. compared the antinociceptive effect of morphine and acetylsalicylic acid to that of four bisphosphonates; i.e., clodronate, alendronate, pamidronate and etidronate. When the various analgesics were injected into the tails of mice, a dose-dependent antinociception was observed with pamidronate, clodronate and acetylsalicylic acid, whereas etidronate and alendronate produce an analgesic effect only at the highest dose tested.

Neither Goicoechea et al. nor Bonabello et al. studied any long term pain antinociceptive effects resulting from the administration of a bisphosphonate.

BRIEF SUMMARY OF THE INVENTION

This invention is directed to a method of treating chronic spinal mechanical pain by intravenously administering to a subject in need of chronic spinal mechanical pain relief an effective amount for treating spinal mechanical pain of bisphosphonate.

DETAILED DESCRIPTION OF THE INVENTION

The present invention is directed to a novel therapeutic use of intravenous bisphosphonate in patients with chronic mechanical back pain due to degenerative disc disease (DDD) and other mechanical causes, i.e. those conditions excluding bone fractures from metastatic disease or osteoporosis. It has now been surprisingly discovered that administering an effective amount of bisphosphonate intravenously to a subject in need of pain relief from chronic spinal mechanical pain results in the subject experiencing prolonged pain relief, going well beyond the period in which the analgesic properties of bisphosphonates such as pamidronate are known to be effective. This new method of treating chronic spinal mechanical pain is simple, effective, does not require chronic administration of drugs and does not require surgery or invasive procedures. This discovery is surprising and unexpected because the analgesic effect of pamidronate has never been reported to last more than 2-3 weeks (and only in patients suffering from bone pain from metastatic cancer). In the present invention, patients receiving bisphosphonate treatment are free of chronic spinal pain for six months or more after treatment. These patients may be considered to have had their spinal pain effectively cured.

Bisphosphonates are synthetic compounds characterized by a P—C—P bond. Bisphosphonate drugs can be divided into two pharmacological classes: the aminobisphosphonates, which act by inhibiting protein isoprenylation; and the less potent non-aminobisphosphonates, which act through the intracellular accumulation of beta-gammamethylene-type analogs of ATP metabolites. Aminobisphosphonates include alendronate ($C_4H_{12}NNaO_7P_2 3H_2O$), ibandronate, pamidronate ($C_3H_9NO_7P_2Na_2 5H_2O$) and zoledronic acid (1-Hydroxy-2-imidazol-1yl-phosphonoethyl) phosphoric acid monohydrate ($C_5H_{10}N_2O_7P_2 \cdot H_2O$) available as Zometa from Novartis, East Hanover, N.J. Non-aminobisphosphonates include etidronate, clodronate, and tiludronate. The preferred bisphosphonate of the present invention is pamidronate. Pamidronate disodium is available as Aredia® from Novartis Pharmaceutical of East Hanover, N.J. in 30 mg or 90 mg vials for injection.

The terms "effective amount" or "therapeutically effective amount" are defined as an amount of the agent (in this case, bisphosphonate) at least sufficient to provide the desired therapeutic effect. (Preferably, nontoxic levels of the active agent will be employed, if possible.) The exact amount required will vary from subject to subject, depending on age, general condition of the subject, the severity of the condition being treated, and the particular active agent administered, and the like.

Except for zoledronic acid, the effective amount of bisphosphonate employed in the present invention ranges from between about 0.5 and 5.4 mg of bisphosphonate/kg of body weight, preferably between about 1.0 and 4.5 mg of bisphosphonate/kg and is most preferably about 3.0 mg of bisphosphonate/kg of body weight. A single dosage (treatment) is generally between 0.5 and 1.8 mg of bisphosphonate/kg of body weight, preferably between 1.0 and 1.5 mg of bisphosphonate/kg of body weight and most preferably 1.2 mg of bisphosphonate/kg of body weight. A preferred single dose of bisphosphonates (other than zoledronic acid) ranges from about 60 mg to about 120 mg, and is most preferably about 90 mg. The effective amount of bisphosphonate can be administered in one or more doses.

The effective amount of zoledronic acid is between 2 and 32 mgs, and this amount can be administered by intravenous injection in one or more divided doses of between 2 and 16 mgs each.

Each dosage of bisphosphonate is preferably administered to the subject by intravenous infusion, over four hours. The method of the invention involves administration of the effective amount in one or more separate doses that can be administered to the patient anywhere from a day to a month apart. In one embodiment of the invention, a single treatment of zoledronic acid (4 mg) is administered to a patient by intravenous infusion. In another embodiment of the invention, a bisphosphonate such as pamidronate is administered by infusion once daily (1.2 mg/kg of body weight per day) for three consecutive days. In another preferred embodiment of the invention, a bisphosphonate such as pamidronate is administered once a week (1.2 mg/kg of body weight at each administration) for three consecutive weeks. In a still further embodiment of the invention, the effective amount of a bisphosphonate, such as pamidronate, is administered to the patient once a month (1.2 mg/kg of body weight at each administration) for three consecutive months.

Depending on the individual patient's age, general condition, severity of disease and the particular bisphosphonate employed, the number of dosages required to achieve effective relief from spinal mechanical pain will vary. In general, at least one treatment (intravenous injection) with zoledronic acid is required to achieve effective relief from spinal mechanical pain, while from one to three treatments at spaced apart intervals may be required with pamidronate and other bisphosphonates.

The term "intravenous" is defined as within or administered into a vein.

Administration of an effective amount of bisphosphonate results in subjects experiencing prolonged relief from chronic mechanical pain. The terms "prolonged pain relief" as used herein are defined as relief from chronic mechanical pain for a duration of more than one month, preferably for 3 months, and more preferably for 6 months.

The term "chronic spinal mechanical pain" is defined as any back pain lasting more than twelve weeks which is not caused by cancer, or an osteoporotic compression fracture. The origin of the chronic spinal mechanical pain may be cryptogenic or idiopathic and is commonly associated with DDD, and degenerative processes (i.e. spondylosis) of the intervertebral spaces and facet joints.

Administration of bisphosphonates may also be employed in the treatment of acute spinal mechanical pain and spinal mechanical pain in post-operative patients.

The term "subject" as used herein is defined as a mammal, preferably a human.

The following example illustrates the invention without limitation.

EXAMPLE

Three subjects, suffering from chronic daily (longer than 1 year) axial mechanical pain of the spine, were given approximately 1.2 mg per kg pamidronate as an intravenous infusion over 4 hours once a day for three consecutive days (total 3.6 mg/kg).

Subject #1 was a 53-year-old-female with DDD and osteopenia. Subject #2 was a 57-year-old-female with DDD and moderate osteoporosis (without compression fractures). Subject #3 was a 43-year-old-female with DDD. The subjects were not affected by any specific cause of axial back pain, including cancer, osteoporotic compression fractures or metastatic disease. The treated subjects did not suffer from osteoporotic compression fractures, Paget's disease, or hypercalcemia of malignancy (HCM).

All three subjects were on combination therapies of anti-inflammatory (NSAID) and opioid medications taken on an as needed basis (PRN) which did not relieve their pain. On the second day of infusion, 2 of the 3 subjects reported myalgias that responded well to anti-inflammatory (NSAID) agents. All subjects showed an increase in their bone density. The subjects did not exhibit any hypocalcemia, cardiac, hepatic or renal impairments. Assessments of axial spinal pain using a numerical scale (0=no pain; 10=the worst pain imaginable) were performed at baseline and at 1 month, 2 month, 4 month, and 6 month follow-up visits. Table 1 illustrates the results.

TABLE 1

| Subject | Baseline | 1 month | 2 months | 4 months | 6 months |
|---------|----------|---------|----------|----------|----------|
| 1 | 8 | 4 | 0 | 0 | 0 |
| 2 | 8-9 | 5 | 0 | 0 | 0 |
| 3 | 5 | 0 | 0 | 0 | 0 |

As shown in Table 1, all three subjects were pain free 6 months after the 3-day therapy with pamidronate. All subjects showed an increase in their bone density at 6 months post-infusion. Of note, at 2 months from initiation of the pamidronate infusion therapy, all subjects discontinued the opioid agents.

Some patients took NSAID's (such as acetaminophen and ibuprofen) sporadically during the post-infusion period (not on a daily basis). It is believed that for these patients the IV pamidronate treatment was responsible for the prolonged improvement and apparent resolution of their pain. The analgesic effect of acetaminophen, ibuprofen and other NSAID's is known to last only a few hours, whereas the pain relieving effects of pamidronate appear to be long lasting i.e. up to 6 or more months.

All patents, applications, articles, publications, and test methods mentioned above are hereby incorporated by reference.

What is claimed is:

1. A method of treating chronic spinal mechanical pain which comprises intravenously administering to a human subject in need of chronic spinal mechanical pain relief an effective amount for relieving chronic spinal mechanical pain of pamidronate, wherein pamidronate provides prolonged pain relief, and the chronic spinal mechanical pain is relieved for at least three months following the administration of pamidronate.

2. The method of claim 1, wherein the effective amount is administered in more than one dose.

3. The method of claim 1 which comprises administering pamidronate by intravenous injection.

4. The method of claim 1, wherein the chronic spinal mechanical pain is of non-osteoporotic compression fracture origin.

5. The method of claim 1, wherein the effective amount of pamidronate ranges from about 0.5 to about 5.4 mg/kg of body weight.

6. The method of claim 1, which comprises administering the effective amount in a single dose.

* * * * *